United States Patent [19]

Fujita et al.

[11] Patent Number: 4,880,572

[45] Date of Patent: Nov. 14, 1989

[54] UN-NATURAL CERAMIDE RELATED COMPOUNDS AND PREPARATION THEREOF

[75] Inventors: Shuji Fujita, Tachikawa; Shoji Yoshimura, Iruma; Masayoshi Ito, Kunitachi; Yoshiyasu Shitori, Tokyo; Tomoya Ogawa, Musashino, all of Japan

[73] Assignee: MECT Corporation, Japan

[21] Appl. No.: 199,107

[22] Filed: May 26, 1988

[30] Foreign Application Priority Data

May 28, 1987 [JP] Japan .................... 61-132696

[51] Int. Cl.$^4$ .................................. C09F 5/00
[52] U.S. Cl. ...................... 260/404; 260/402; 260/405; 260/405.5; 549/365; 549/369
[58] Field of Search ............................. 260/404

[56] References Cited

FOREIGN PATENT DOCUMENTS 63-104986  5/1988  Japan .

OTHER PUBLICATIONS

Patent Abstracts of Japan, Japanese Application 59-44913 (1985).

Chemical Abstracts, Formula Index, Jul.–Dec., 1987, p. 3424F, col. 1, lines 31–34.
Chemical Abstracts, vol. 52, C. A. Grob et al., Abstract 7202h–7204e (1958).
Chemical Abstracts, vol. 107, T. Ogawa et al., Abstract 154687u (1987).

Primary Examiner—Paul J. Killos
Attorney, Agent, or Firm—Jacobs & Jacobs

[57] ABSTRACT

Novel unnatural ceramide related compounds, for instance, (2S, 3S)-2-tetracosanamido-octadecane-1,3-diol are herein provided, which are useful as intermediates in preparing ceramide moieties employed in the preparation of glycolipids and gangliosides known as tumor markers or molecular markers and which are prepared by, for instance, subjecting a chiral compound represented by the following formula:

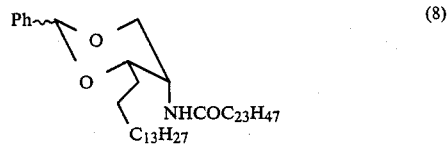

to deacetal treatment.

17 Claims, No Drawings

UN-NATURAL CERAMIDE RELATED COMPOUNDS AND PREPARATION THEREOF

BACKGROUND OF THE INVENTION

1. Field of the Invention

The present invention relates to unnatural ceramide related compounds and more particularly to unnatural ceramide related compounds useful as intermediates for the preparation of sphingoglycolipids. The present invention also relates to a method for preparing the ceramide related compounds.

2. Description of the Prior Art

The glycolipid of mammalian cells belongs to the category of so-called sphingoglycolipid and comprises (i) a lipid structure referred to as ceramide composed of a long-chain aminoalcohol called sphingosine to which a fatty acid is amido-bonded and (ii) various combinations of sugars selected from the group consisting of glucose, galactose, N-acetylglucosamine, N-acetylgalactosamine, fucose and sialic acid which are bonded to the structure through glycoside bonds. Among these, the glycolipids carrying sialic acids are called gangliosides.

Most of these compounds are generally located in the outerside layer of the double layer of cell membrane and it has been thought from recent investigations that these compounds play important roles in the functions as a reception, response and receptor of recognition and information, differentiation, proliferation, malignant change, or behavior of cells.

However, it is quite difficult to isolate such sphingoglycolipids from an organism and to purify it. Therefore, the precise synthesis of the aforementioned ceramide related compounds is necessary and indispensable for the elucidation of the relationship between the precise biological information of these sugar chains and the molecular structure thereof.

Under such circumstances, the inventors of this invention have already developed a method for stereospecifically preparing these glycolipids, in particular natural ceramide moieties in a good yield (see Japanese Patent Un-examined Publication, hereunder referred to as "J. P. KOKAI" for simplicity, No. 60-190745).

Moreover, the natural sphingosine is an optically active compound of D-series (2S, 3R) of erythro arrangement and various methods for preparing the same have presently been proposed, in which D-glucose or L-serine is used as a starting material.

Moreover, there has been proposed, by Grob C. A. (Helv. Chim. Acta, 1957, Vol. 40, p. 1145), a method for preparing an unnatural ceramide such as a trans-DL-threo isomer or a cisDL-threo isomer in which an achiral compound is used as a starting material.

However, in the conventional methods, all the processes for obtaining final products, i.e., unnatural and natural ceramides, are carried out using materials in the form of racemate forms, although the optical resolution of the final products is very difficult.

SUMMARY OF THE INVENTION

Accordingly, it is a purpose of the present invention to provide new unnatural ceramide related compounds serving as intermediates useful in synthesizing gangliosides and a method for efficiently preparing the compounds.

The inventors of the present invention have conducted various studies to eliminate the aforementioned drawbacks associated with the conventional methods and have succeeded to prepare new optically active unnatural ceramides without a process for optical resolution by using chiral compounds instead of achiral compounds as the starting compounds for the foregoing methods for preparing the same.

Thus, the present invention relates to an unnatural ceramide related compound represented by the formulas (I) or (II):

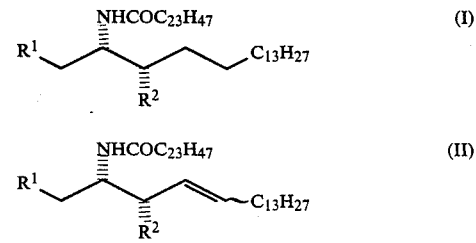

wherein $R^1$ and $R^2$ are independently hydroxyl group, acetoxy group or 1-ethoxyethyloxy group. Examples of the compound represented by the formula (I) include (A) (2S, 3S)-2-tetracosanamido-octadecane-1,3-diol. Examples of the compound represented by the formula (II) include (B) (2S, 3S, 4E)-2-tetracosanamido-1,3-0-bis(1-ethoxyethyl)-4-octadecene-1,3-diol; (C) (2S, 3S, 4Z)-2-tetracosanamido-1,3-0-bis(1-ethoxyethyl)-4-octadecene-1,3-diol; (D) (2S, 3S, 4E)-2-tetracosanamido-1,3-di-0-acetyl-4-octadecene-1,3-diol; (E) (2S, 3S, 4Z)-2-tetracosanamido-1,3-di-0-acetyl-4-octadecene-1,3-diol; (F) (2S, 3S, 4E)-2-tetracosanamido-4-octadecene-1,3-diol; and (G) (2S, 3S, 4Z)-2-tetracosanamido-4-octadecene-1,3-diol.

According to another aspect of the present invention, there is provided a method for preparing an unnatural ceramide related compound ((2S, 3S)-2-tetracosanamido-octadecane-1,3-diol) represented by the following formula:

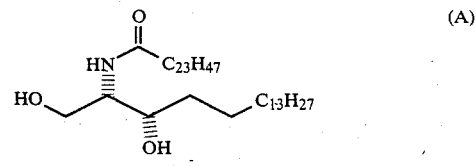

comprises subjecting a compound represented by the formula

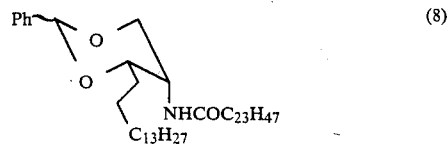

to deacetal treatment.

According to a further aspect of the present invention, there is provided a method for preparing (2S, 3S)-2-tetracosanamido-octadecane-1,3-diol represented by the formula:

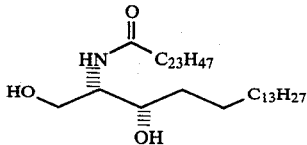

(A)

comprises subjecting a compound represented by the formula:

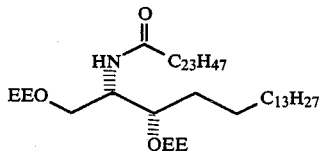

(13)

(wherein EE represents a 1-ethoxyethyl group) to deethoxyethylation.

The present invention further provides a method for preparing (2S, 3S, 4E)-2-tetracosanamido-4-octadecene-1,3-diol represented by the formula:

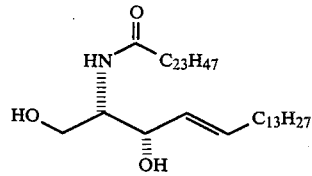

(F)

and (2S, 3S, 4Z)-2-tetracosanamido-4-octadecene-1,3-diol represented by the formula:

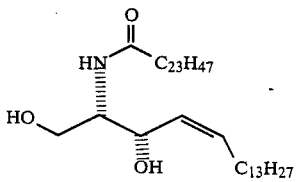

(G)

comprises acetylating (2S, 3S)-2-tetracosanamido-4-octadecene-1,3-diol represented by the formula:

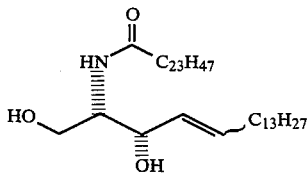

(16)

to protecting the same, then separating the products into (2S, 3S, 4E)-2-tetracosanamido-1,3-di-0-acetyl-4-octadecene-1,3-diol represented by the formula:

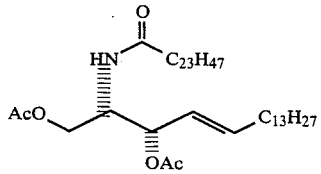

(D)

and (2S, 3S, 4Z)-2-tetracosanamido-1,3-di-0-acetyl-4-octadecene-1,3-diol represented by the formula:

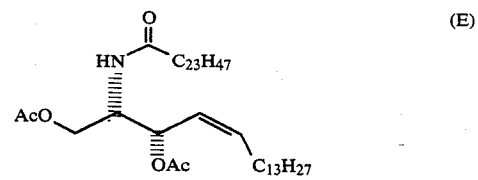

(E)

and then deacetylating these products.

Compounds A, F and G of the present invention are intermediates that may be used in the production of synthetic gangliosides GM1, GM2 and GM3, while compounds B, C, D and E of the invention are intermediates that may be used in Scheme (III), which is described in detail hereinafter, for the production of compounds F and G.

Gangliosides GM1, GM2 and GM3 are important as regulatory factors for the differentiation of the central nervous system. Protein Nucleic Acid and Enzyme, 29 (12) 1146-1159 (1984). For example, GM1 is known as a receptor of cholera toxin Biochemistry, 12, 3547-3558) (1973), and GM3 is known as a regulatory factor or receptor of fibroblost growth factor (FGF). (Biochem. Biophys. Res. Commun., 106 711-718 (1982).

Synthetic gangliosides are also useful in research on the function and specificity of gangliosides and the mechanism of diseases due to disorders in the differentiation of the central nervous system. Such research is conducted by comparing synthetic gangliosides with natural gangliosides.

Gangliosides GM1, GM2 and GM3 may be prepared from compounds A, F and G according to the schemes A to D below.

Firstly, as shown in scheme A, a hydroxy group of compounds A, F and G is converted into a benzoyl group (A-3, F-3 and G-3), respectively, by a conventional method comprising reacting a compound A (F or G) with trityl chloride in pyridine, reacting the resulting trityl compound A-1 (F-1 or G-1) with benzoyl chloride in dimethylaminopyridine and treating the resulting trityl-benzoyl compound A-2 (F-2 or G-2) with p-toluenesulfonic acid to remove the trityl group and form a benzoyl compound A-3 (F-3 or G-3).

Preparation of synthetic gangliosides GM1, GM2 and GM3 can be carried out by the methods described in M. Sugimoto et al, Carbohydrate Research, 156 (1986) c1-c5, "Total synthesis of ganglioside GM1 and GM2" and M. Sugimoto et al, Glycoconjugate J. (1985) 2, 5-9, "Synthesis of a Hematoside (GM3-ganglioside) and a Stereoisomer" (see schemes B, C and D). Synthetic ganglioside GM1 (GM2 or GM3) is prepared by reacting compound A-3 (F-3 or G-3) with a sugar compound in the presence of a glicosidation catalyst at a temperature from −20° to 60° C. for 2 to 12 hours and treating the resulting compound with NaOCH$_3$ to remove protecting groups such as benzoyl. A Lewis acid catalyst, such as BF$_3$—Et$_2$O, TMS triflate (TMS : trimethyl silane) and AlCl$_3$, may be used as a glicosidation catalyst.

Scheme A
compound (A) →
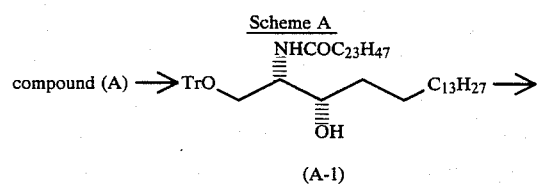
(A-1)
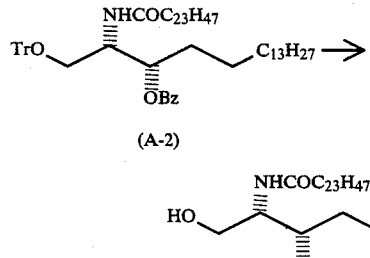
(A-2)
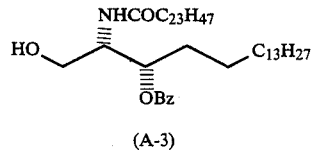
(A-3)
(Bz = Benzoyl)
compound (F) →
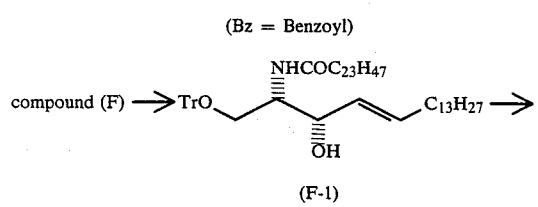
(F-1)
-continued
Scheme A
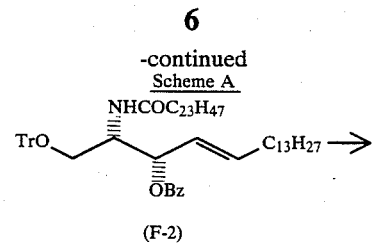
(F-2)
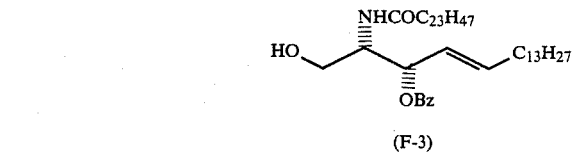
(F-3)
compound (G) →
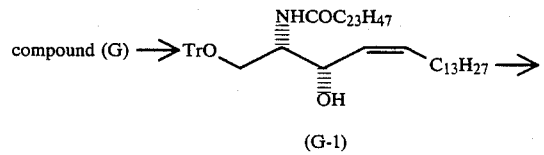
(G-1)
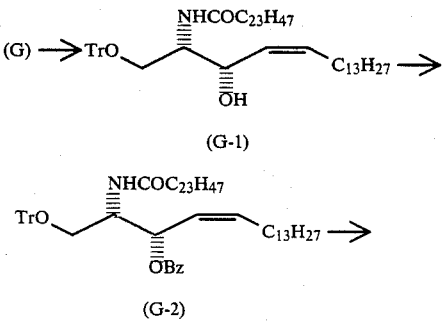
(G-2)
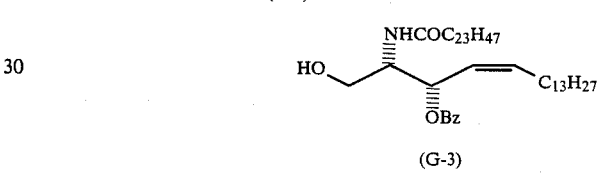
(G-3)
Scheme B
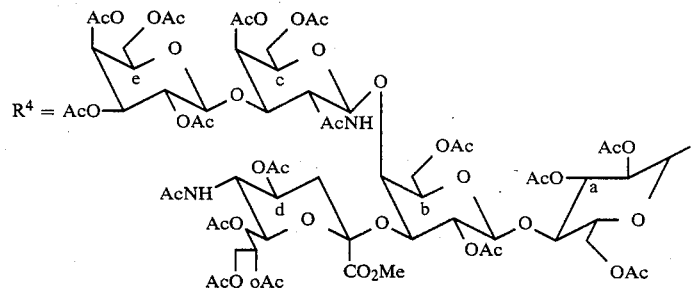
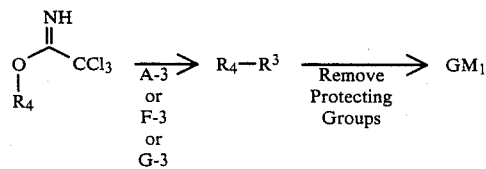
Compound    $R^3$
A-3
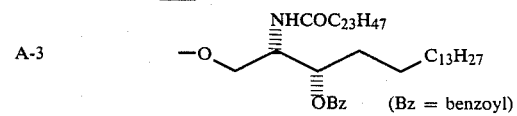
(Bz = benzoyl)
F-3
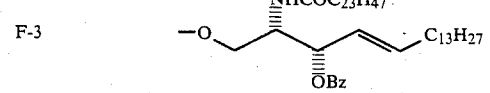

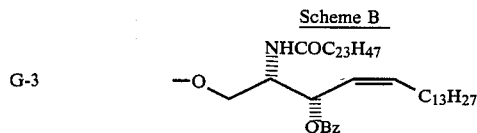
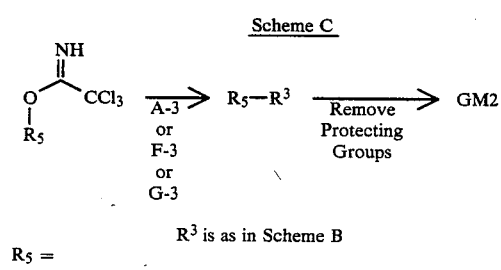
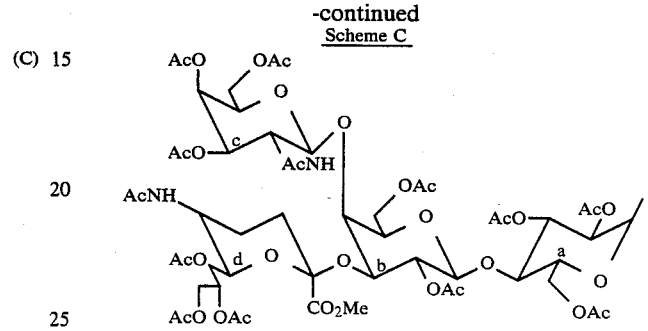
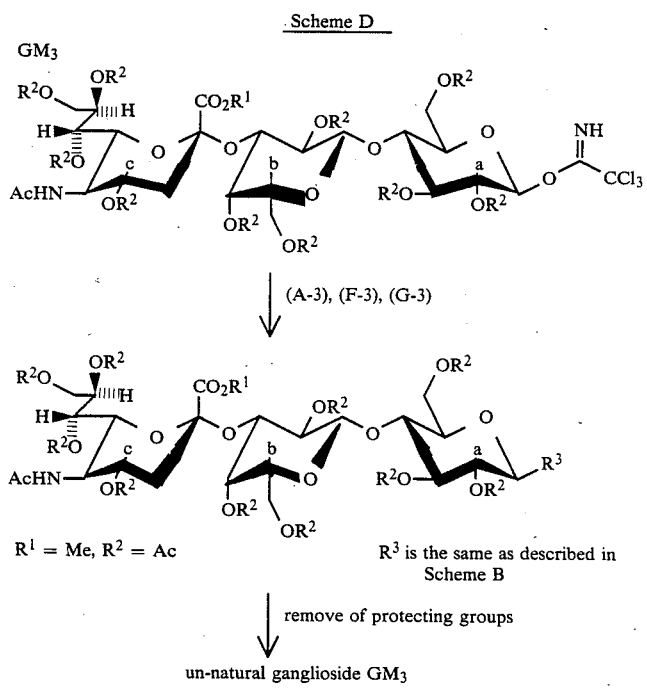
DETAILED EXPLANATION OF THE INVENTION
The present invention will hereunder be explained in more detail on the basis of the following reaction schemes (I) to (III):

Scheme (I)
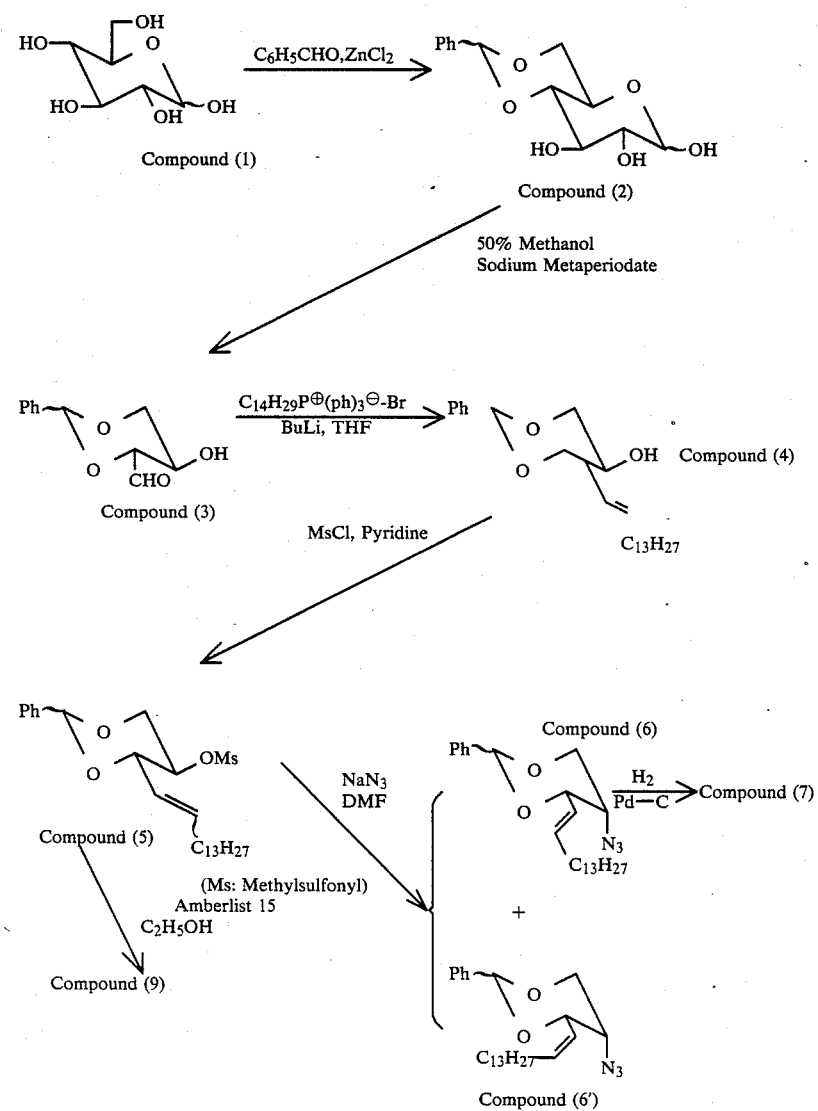
Scheme (II)
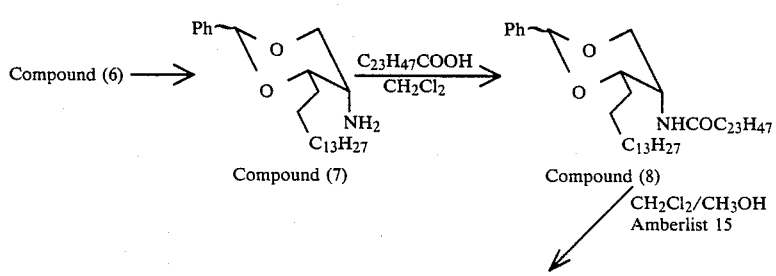

-continued
Scheme (II)
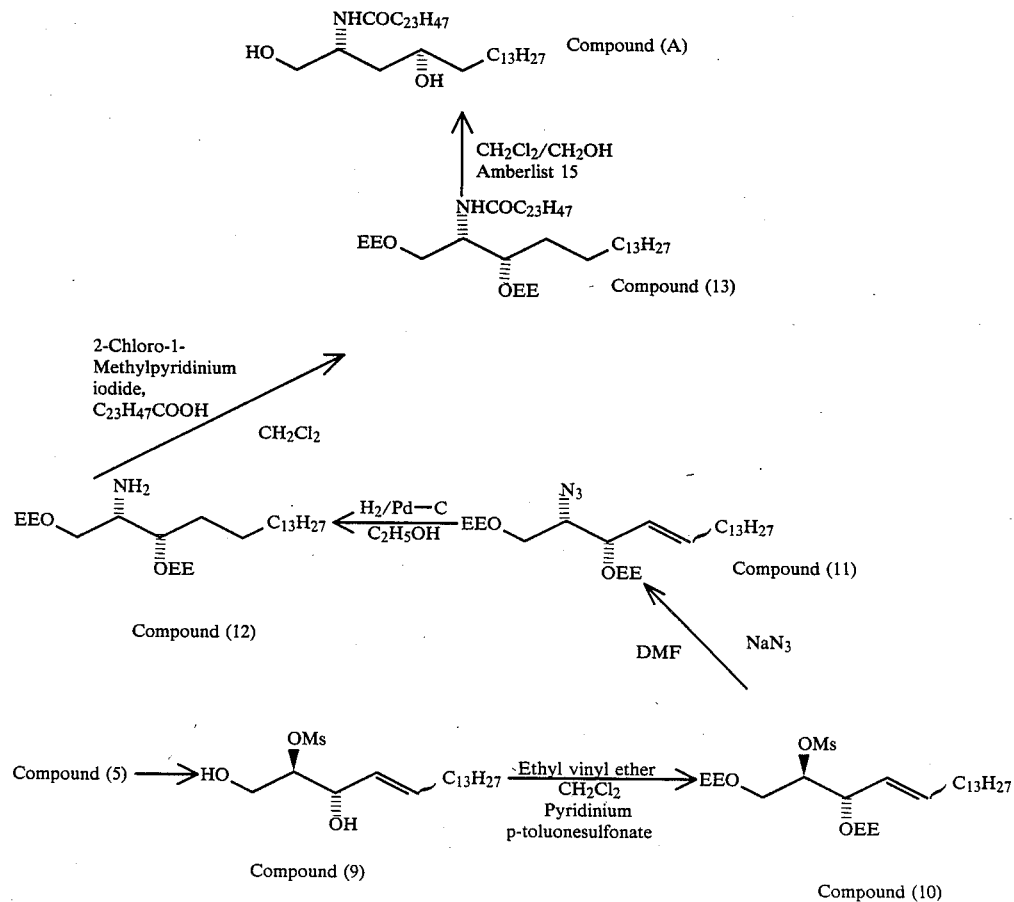
Scheme (III)
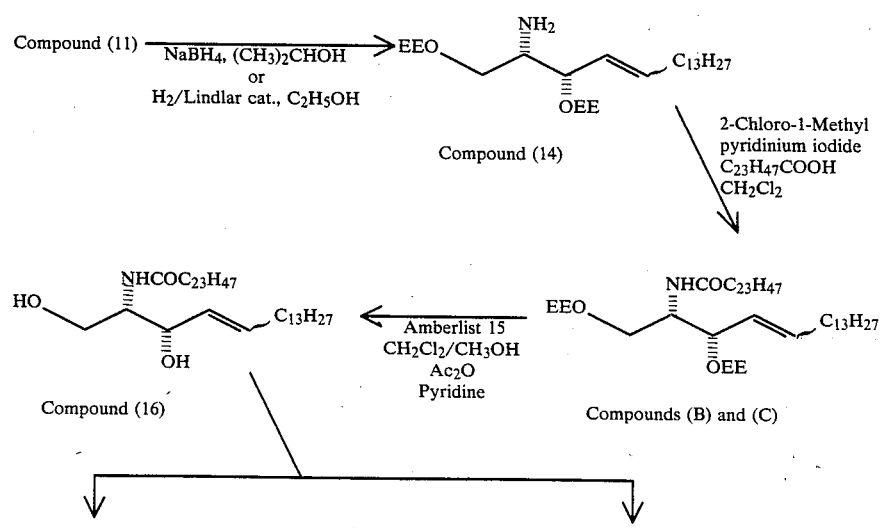

Scheme (III) -continued

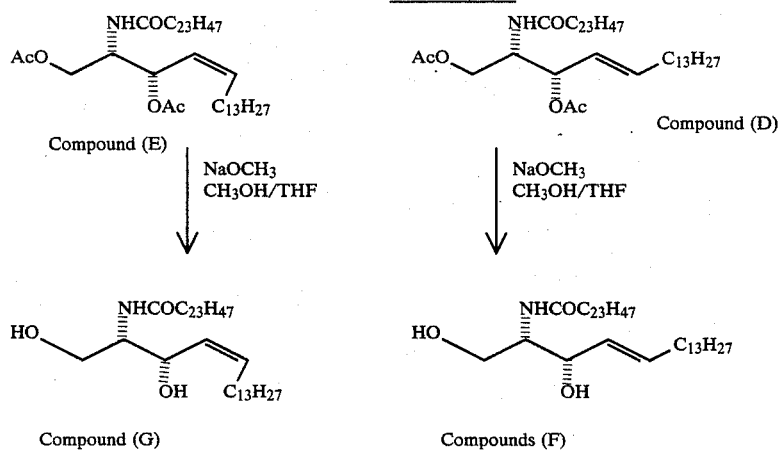

Compound (E)            Compound (D)

↓ NaOCH₃ CH₃OH/THF     ↓ NaOCH₃ CH₃OH/THF

Compound (G)         Compounds (F)

(a) Preparation of Compound (2)

Compound (2) can be prepared by reacting compound (1) under the following reaction conditions:

In this reaction, ZnCl$_2$ can be used as a catalyst. In addition, benzaldehyde or dimethoxytoluene, preferably benzaldehyde may be used as a reagent. This reaction may be carried out at a temperature of about 15° to about 50° C., preferably room temperature for about 6 to about 36 hours, preferably about 12 hours while stirring. The resulting product is purified according to a usual manner such as recrystallization.

(1) Preparation of Compound (3)

Compound (3) can be prepared by reacting compound (2) under the following reaction conditions:

In this reaction, sodium metaperiodate can be used as a catalyst. In addition, methanol, preferably 50% methanol may be used as a solvent. This reaction may be carried out at a temperature of about 10° to about 50° C., preferably room temperature for about 1 to about 8 hours, preferably about 4 hours while stirring.

(2) Preparation of Compound (4)

Compound (4) can be prepared by reacting compound (3) with $C_{14}H_{29}P^+(Ph)_3{}^-$—Br under the following reaction conditions:

In this reaction, n-butyl lithium or phenyl lithium, preferably n-butyl lithium can be used as a catalyst. In addition, tetrahydrofuran (THF) or hexane, preferably THF may be used as a solvent. This reaction may be carried out at temperatures of about −30° to about −15° C., preferably about −20° C. for about 0.5 to about 24 hours, preferably about 20 hours while stirring. The reaction product thus obtained is purified by any conventional technique such as column chromatography.

(3) Preparation of Compound (5)

Compound (5) can be prepared by methylsulfonylating compound (4) under the following reaction conditions:

In this reaction, pyridine may be used as a solvent. This reaction may be carried out at temperatures of about 0° to about 25° C., preferably about 20° C. for about 2 to about 30 hours, preferably about 20 hours while stirring. The reaction product thus obtained is purified by any conventional technique such as column chromatography.

(4) Preparation of Compounds (6) and (6′)

Compound (6) or (6′) can be prepared by converting compound (5) to azide derivative thereof under the following reaction conditions:

In this reaction, dimethyl formamide (DMF) may be used as a solvent. This reaction may be carried out at a temperature of about 70° to about 120° C., preferably about 110° C. for about 1 to about 6 days, preferably about 4 days while stirring. The reaction product thus obtained is purified by any conventional technique such as column chromatography.

(5) Preparation of Compound (7)

Compound (7) can be prepared by hydrogenating compound (6) under the following reaction conditions:

In this reaction, Lindlar catalyst or carbon carrying palladium (Pd-C), preferably Pd-C may be used as a catalyst. In addition, methanol, ethanol or isopropyl alcohol, preferably ethanol may be used as a solvent. This reaction may be carried out at a temperature of about 15° to about 25° C., preferably about 20° C. and a hydrogen pressure of 0.5 to 4 atm. preferably 1 atm. for about 5 to about 20 hours, preferably about 7 hours while stirring. The reaction product thus obtained is purified by any conventional technique such as column chromatography.

(6) Preparation of Compound (8)

Compound (8) can be prepared by reacting compound (7) with lignoceric acid ($C_{23}H_{47}COOH$) under the following reaction conditions:

In this reaction, dichloromethane, chloroform or dichloroethane, preferably dichloromethane may be used as a solvent for the reagent. This reaction may be carried out at the reflux temperature of the solvent used for about 0.5 to about 13 hours, preferably about 3 hours while stirring. The reaction product thus obtained is purified by any conventional technique such as column chromatography.

(7) Preparation of Compound (A)

Compound (A) can be prepared by subjecting the compound (8) to deacetal treatment under the following reaction conditions:

In this reaction, p-toluenesulfonic acid, hydrochloric acid or Amberlist 15, preferably Amberlist 15 may be used as a catalyst. In addition, dichloromethane/methanol, chloroform/methanol or THF/methanol preferably dichloromethane/methanol may be used as a solvent. This reaction may be carried out at the reflux temperature of the solvent used for about 5 to about 30 hours, preferably about 28 hours while stirring. The reaction product thus obtained is purified by any conventional technique such as recrystallization.

(8) Preparation of Compound (9)

Compound (9) can be prepared by subjecting compound (5) to deacetal treatment under the following reaction conditions:

In this reaction, p-toluenesulfonic acid, hydrochloric acid or Amberlist 15, preferably Amberlist 15 may be used as a catalyst. In addition, methanol or ethanol, preferably ethanol may be used as a solvent. This reaction may be carried out at a temperature of about 60° to about 80° C., preferably about 65° C. for about 5 to about 15 hours, preferably about 8 hours while stirring. The reaction product thus obtained is purified by any conventional technique such as column chromatography.

(9) Preparation of Compound (10)

Compound (10) can be prepared by reacting compound (9) with ethyl vinyl ether ($C_2H_5OCH=CH_2$) under the following reaction conditions:

In this reaction, pyridinium p-toluenesulfonate may be used as a catalyst. In addition, dichloroethane, dichloromethane or chloroform, preferably dichloromethane may be used as a solvent. This reaction may be carried out at a temperature of about 0° to about 30° C., preferably about 20° C. for about 0.5 to about 24 hours, preferably about 1 hour while stirring. The reaction product thus obtained is purified by any conventional technique such as column chromatography.

(10) Preparation of Compound (11)

Compound (11) can be prepared by converting compound (10) to azide derivative thereof under the following reaction conditions:

In this reaction, DMF may be used as a solvent. This reaction may be carried out at a temperature of about 70° to about 120° C., preferably about 110° C. for about 1 to about 6 days, preferably about 4 days while stirring. The reaction product thus obtained is purified by any conventional technique such as column chromatography.

(11) Preparation of Compound (12)

Compound (12) can be prepared by hydrogenating compound (11) under the following reaction conditions:

In this reaction, Lindlar catalyst of Pd-C, preferably the latter may be used as a catalyst. In addition, methanol or ethanol, preferably ethanol may be used as a solvent. This reaction may be carried out at a temperature of about 15° to about 25° C., preferably about 20° C. and a hydrogen pressure of 1 to 4 atms., preferably about 1 atm. for about 5 to about 20 hours, preferably about 7 hours while stirring. The reaction product thus obtained is purified by any conventional technique such as column chromatography.

(12) Preparation of Compound (13)

Compound (13) can be prepared by reacting compound (12) with lignoceric acid ($C_{23}H_{47}COOH$) under the following reaction conditions:

In this reaction, dichloromethane, chloroform or dichloroethane, preferably dichloromethane may be used as a solvent. This reaction may be carried out at the reflux temperature of the solvent used for about 0.5 to about 13 hours, preferably about 3 hours while stirring. The reaction product thus obtained is purified by any conventional technique such as column chromatography.

(13) Preparation of Compound (A)

Compound (A) can be prepared by reacting compound (13) under the following reaction conditions:

In this reaction, Amberlist 15 or p-toluenesulfonic acid, preferably Amberlist 15 may be used as a catalyst. In addition, dichloromethane/methanol, chloroform/methanol or THF/methanol, preferably dichloromethane/methanol may be used as a solvent. This reaction may be carried out at a temperature of about 0° to about 30° C., preferably about 20° C. for about 5 to about 20 hours, preferably about 10 hours while stirring. The reaction product thus obtained is purified by any conventional technique such as column chromatography.

(14) Preparation of Compound (14)

Compound (14) can be prepared by hydrogenating compound (11) under the following reaction conditions:

In this reaction, sodium borohydride ($NaBH_4$), may be used as a catalyst. In addition, ethanol or isopropyl alcohol, preferably isopropyl alcohol may be used as a solvent. This reaction may be carried out at a reflux temperature of the solvent used for about 1 to about 6 days, preferably about 2 days while stirring. The reaction product thus obtained is purified by any conventional technique such as column chromatography.

(15) Preparation of Compound (14)

Compound (14) can be prepared by hydrogenating compound (11) under the following reaction conditions:

In this reaction, Lindlar catalyst may be used as a catalyst. In addition, ethanol or methanol, preferably ethanol may be used as a solvent. This reaction may be carried out at a temperature of about 0° to 30° C., preferably 20° C. under a hydrogen pressure of 1 to 4 atm., preferably 1 atm. for about 2 to about 24 hours, preferably about 3 hours while stirring. The reaction product thus obtained is purified by any conventional technique such as column chromatography.

(16) Preparation of Compounds (B) and (C)

Compounds (B) and (C) can be prepared by reacting compound (14) with lignoceric acid ($C_{23}H_{47}COOH$) under the following reaction conditions:

In this reaction, dichloromethane, chloroform or dichloroethane, preferably dichloromethane may be used as a solvent. This reaction may be carried out at the reflux temperature of the solvent used for about 0.5 to about 13 hours, preferably about one hour while stirring. The reaction product thus obtained is purified by any conventional technique such as column chromatography.

(17) Preparation of Compound (16)

Compound (16) can be prepared by eliminating the protective groups from the foregoing compounds (B) and (C) under the following reaction conditions:

In this reaction, Amberlist 15 or p-toluenesulfonic acid, preferably Amberlist 15 may be used as a catalyst. In addition, dichloromethane/methanol, chloroform/methanol or THF/methanol, preferably dichloromethane/methanol may be used as a solvent. This reaction may be carried out at a temperature of about 0° to about 30° C., preferably about 20° C. for about 5 to about 24 hours, preferably about 21 hours while stirring. The reaction product thus obtained is purified by any conventional technique such as recrystallization.

(18) Preparation of Compounds (D) and (E)

Compounds (D) and (E) can be prepared by acetylating compound (16) under the following reaction conditions:

In this reaction, pyridine may be used as a solvent. This reaction may be carried out at a temperature of about 0° to about 30° C., preferably 20° C. for about 1 to about 10 hours, preferably about 2 hours while stirring. The reaction product thus obtained is purified by any conventional technique such as column chromatography.

(19) Preparation of Compound (F)

Compound (F) can be prepared by deacetylating compound (D) under the following reaction conditions:

In this reaction, sodium methoxide (NaOCH$_3$) may be used as a catalyst. In addition, dichloromethane/methanol or THF/methanol, preferably THF/methanol may be used as a solvent. This reaction may be carried out at a temperature of about 0° to about 30° C., preferably about 20° C. for about 0.5 to about 5 hours, preferably about 2 hours while stirring. The reaction product thus obtained is purified by any conventional technique such as recrystallization.

(20) Preparation of Compound (G)

Compound (G) can be prepared by deacetylating compound (E) under the following reaction conditions:

In this reaction, NaOCH$_3$ may be used as a catalyst. In addition, dichloromethane/methanol or THF/methanol, preferably THF/methanol may be used as a solvent. This reaction may be carried out at a temperature of about 0° to about 30° C., preferably about 20° C. for about 0.5 to about 5 hours, preferably about 2 hours while stirring. The reaction product thus obtained is purified by any conventional technique such as recrystallization.

The aforementioned novel ceramide related compounds according to the present invention can very effectively be used in the preparation of ceramide moieties which are employed in preparing glycolipids and gangliosides which are known as tumor markers, molecular markers for cells having the ability of differential induction.

The present invention will hereunder be described in more detail with reference to the following Examples and Reference Examples.

Reference Example 1:

Preparation of Compound (2), (4,6-0-benzylidene-D-glucose)

To 80 g (0.44 moles) of compound (1) were added one liter (8.5 moles) of benzaldehyde and 320 g (2.4 moles) of zinc chloride and then the resultant mixture was vigorously stirred at room temperature overnight.

Then, 1.5 liters of water was added to the reaction solution, followed by stirring the solution for one hour, removing the resultant precipitates by passing through a filter, washing the precipitates with n-pentane and drying in vacuo to obtain 19.81 g of white powder.

The filtrate was extracted with ether, and the extract was washed with saturated NaCl solution and dried over anhydrous magnesium sulfate and concentrated was to give 70.74 g of pale yellow residue. The white powder and the pale yellow residue were combined together and recrystallized from ethanol to thereby obtain 74.26 g (yield=62.8%) of compound (2) as colorless needles.

Physical Properties of Compouns (2)

TLC (silica gel/chloroform-methanol (7:1)): Rf=0.31

M.P.=149°-153° C. (Lit[1]) M.P.=155°-161° C.)

IR$\nu^{KBr}_{max}$cm$^{-1}$: 3582, 3316, 1452

1387, 1367, 1094

1008

Reference (1): Methods in Carbohyde. Chem., 1963, Vol. 2, p 307;

Reference Example 2: Preparation of Compound (3), (2,4-0-benzylidene-D-erythrose)

Compound (2) (13.4 g; 0.05 moles) was dissolved in 150 ml of 50% methanol/water, 42.78 g (0.2 moles) of sodium metaperiodate was added under argon atmosphere at 0° C. and then the mixture was stirred at room temperature for 4 hours. Then, the reaction mixture was filtered and the filtrate was evaporated to dryness under a reduced pressure, the resultant residue was dissolved in 200 ml of chloroform, washed with 10% sodium hydrogen sulfite solution and then with saturated NaCl solution and dried over anhydrous sodium sulfate. The solvent was evaported off in vacuo to obtain 10.08 g (yield=96.2%) of compound (3) as white powder. The product thus obtained was used in the subsequent process without further purification.

Physical Properties of Compounds (3)

TLC (silica gel/chloroform-methanol (10:1)): Rf=0.44; 0.58

IR$\nu^{KBr}_{max}$cm$^{-1}$: 3518, 3436, 1745, 1722, 1385, 1321, 1234, 1205, 1089, 1072, 1031

Reference Example 3: Preparation of Compound (4) ((2R, 3S)-1,3-0-benzylidene-4-octadecene-1,2,3-triol)

To a stirred solution of triphenyltetradecyl phosphonium bromide (21.58 g, 40 mmol) in 60 ml dry THF, was added 22.4 ml (35 mmol) of 1.56 N butyl lithium solution under cooling in an ice-methanol bath (about −20° C.) and the resultant mixture was stirred at that temperature for one hour. Then, 2.08 g (10 mmoles) of compound (3) in 15 ml of THF was dropwise added to the reaction mixture and the solution was stirred overnight.

The reaction solution was evaporated to dryness under reduced pressure, the resulting residue was dissolved in 100 ml of chloroform, followed by washing with water and saturated NaCl solution, drying over anhydrous magnesium sulfate and concentrated in vacuo. The resultant residue was purified by flush chromatography (200 g of Wako gel C-200, eluent: hexane/ethyl acetate=9/1) to obtain 3.11 g (yield=80.2%) of compound (4) as white powder.

Physical Properties of Compound (4)

TLC (silica gel/hexane-ethyl acetate (8:3)): Rf=0.55,

IR$\nu^{KBr}_{max}$cm$^{-1}$: 3470, 2920, 2840, 1465, 1390, 1115, 2070, 1025

Elemental Analysis (as C$_{25}$H$_{40}$O$_3$)

Calculated: C, 77.27; H, 10.37

Found: C, 77.13; H, 10.56

$^1$H-NMR (500MHz, CDCl$_3$+D$_2$O, TMS)δ:

0.880 (t, J=7.0 Hz, —CH$_3$), 1.20–1.42 (m, —(CH$_2$)$_n$—), 2.10 (q, J=7.0 Hz, 6-H, H'trans), 2.10–2.30 (m, 6-H, H'cis), 3.59–3.72 (m, 1-H, 2-H), 3.94–4.00 (m, 3-H), 4.33–4.40 (m, 1-H'), 5.477 (ddt, J=11.0, 9.0, 1.5 Hz 4-Hcis), 5.534 (s,

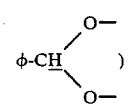

5.556 (ddt, J=15.4, 7.3, 1.5 Hz, 4-Htrans), 5.827 (dt, J=11.0, 7.7 Hz, 5-Hcis), 5.943 (dt, J=15.4, 6.9 Hz, 5-Htrans), 7.33–7.40 (m, phenyl-H), 7.49–7.51 (m, phenyl-H), The ratio of the content of 4-trans-form to that of 4-cis-form of compound (4) was estimated to be 4.21/1.0 from the integrated intensity of NMR peak of 5-H.

Reference Example 4: Preparation of Compound (5) ((2R, 3S)-1,3-0-benzylidene-2-0-methylsulfonyl-4-octadecene-1,2,3-triol)

Compound (4) (1.94 g; 5 mmoles) was dissolved in 5 ml of anhydrous pyridine, and 0.58 ml (7.5 mmoles) of methanesulfonyl chloride was added and stirred under cooling in an ice-methanol bath (about −15° C.) followed by gradually raising temperature to room temperature and stirred overnight. Then, 1 ml of water was added to the reaction mixture, and concentrated the solution under reduced pressure. Residue was dissolved in 50 ml of ether and washed with water and saturated NaCl solution, then dried over anhydrous magnesium sulfate and evaporated in vacuo. The resultant residue (2.5 g) was purified by flush chromatography (110 g of Wako gel C-300, eluent: hexane/ethyl acetate =10/1) to obtain 2.23 g (yield=95.7%) of compound (5) as white powder.

Physical Properties of Compound (5)
TLC (silica gel/hexane-ethyl acetate (4:1)): Rf=0.34
IR$\nu^{KBr}_{max}$cm$^{-1}$: 2920, 2840, 1465,
1340, 1180, 1080,
970
Elemental Analysis (for $C_{26}H_{42}O_5S$),
Claculated: C, 66.92; H, 9.07,
Found: C, 66,86; H, 9.10
$^1$H-NMR (500MHz, CDCl$_3$, TMS)δ:
0.879 (t, J=7.0 Hz, CH$_3$−)
1.20–1.41 (m, —(CH$_2$)$_n$—)
2.084 (q, J=6.9 Hz, 6-H, H')
2.995 (s, CH$_3$SO$_2$−trans)
2.998 (s, CH$_3$SO$_2$−cis)
3.844 (dd, J=10.3, 9.8 Hz, 1-Htrans)
4.194 (dd, J=9.8, 7.3 Hz, 3-Htrans)
4.488 (dt, J=9.8, 9.8 Hz, 2-Htrans)
4.536 (dd, J=10.3, 5.3 Hz, 1-Htrans)
5.512 (dd, J=11.0, 8.8 Hz, 4-Hcis), 5.546 (s,

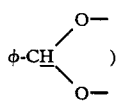

5.537 (dd, J=15.4, 7.3 Hz, 4-Htrans) 5.828 (dt, J=11.0, 7.7 Hz, 5-Hcis) 5.962 (dt, J=15.4, 7.0 Hz, 5-Htrans) 7.35–7.39 (m, phenyl-H) 7.46–7.49 (m, phenyl-H)

The ratio of the content of 4-trans-form to that of 4-cis-form of compound (5) was estimated to be 3.6/1.0 from the integrated intensity of NMR peak of 5-H.

Reference Example 5: Preparation of Compounds (6) and (6') ((2S, 3S, 4E)-2-azido-1,3-0-benzylidene-4-octadecene-1,3-diol (6) and (2S, 3S, 4Z)-2-azido-1,3-0-benzylidene-4-octadecene-1,3-diol(6'))

Compound (5) (3.45 g; 7.4 mmoles) was dissolved in 35 ml of anhydrous DMF and 2.89 g (44.5 mmoles) of sodium azide was added and the mixture was heated to 100° to 110° C. for 102.5 hours in an oil bath. The reaction solution was concentrated in vacuo, the resulting residue was dissolved in ether, washed with 5% aqueous solution of sodium bicarebonate, water and saturated NaCl solution and dried over anhydrous magnesium sulfate. The brown product (2.78 g) obtained after evaporating off the solvent in vacuo was purified by flush chromatography (110 g of Wako gel C-300; eluent: hexane/ethyl acetate=15/1) to obtain 1.15 g (yield=37.6%) of compound (6) (trans-form) and 0.35 g (yield=11.4%) of compound (6') (cis-form). The compound (6) was recrystallized from n-pentane to obtain colorless needles.

Physical Properties of Compound (6)
TLC (silica gel/hexane-ethyl acetate (4:1)): Rf=0.44
M.P.=45°–45.5° C.
IR$\nu^{heat}_{max}$cm$^{-1}$: 2920, 2850, 2100,
1450, 1395, 1120,
1085
Elemental Analysis (for $C_{25}H_{39}N_3O_2$),
Claculated: C, 72.60; H, 9.50; N, 10.16,
Found: C, 72.44; H, 9.49; N, 10.19
$^1$H-NMR (400MHz, CDCl$_3$, TMS)δ:
0.878 (3H, t, J=6.8 Hz, —CH$_3$),
1.20–1.35 (20H, m, —CH$_2$×10),
1.35–1.45 (2H, m, 7-H, H'),
2.094 (2H, q, J=6.9 Hz, 6-H, H'),
2.946 (1H, broad s, 2-H),
4.240 (1H, dd, J=12.2, 2.0 Hz, 1-H),
4.481 (1H, dd, J=12.2, 2.0 Hz, 1-H'),
4.569 (1H, d, J=6.4 Hz, 3H),
5.649 (1H, s,

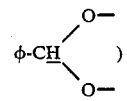

5.677 (1H, dd, J=16.1, 6.4 Hz, 4-H),
5.908 (1H, dd, J=16.1, 6.8 Hz, 5-H), 7.36–7.40 (3H, m, phenyl-H), 7.52–7.55 (2H, m, phenyl-H), Physical Properties of Compound (6')
TLC (silica gel/hexane-ethyl acetate (4:2)): Rf=0.51
IR$\nu^{heat}_{max}$cm$^{-1}$: 2920, 2850, 2100,
1455, 1395, 1300,
1150
Elemental Analysis (for $C_{25}H_{39}N_3O_2$),
Claculated: C, 72.60; H, 9.50; N, 10.16,
Found: C, 72.45; H, 9.47; N, 10.15
$^1$H-NMR (400MHz, CDCl$_3$, TMS)δ:
0.883 (3H, t, J=6.8 Hz, —CH$_3$),
1.20–1.35 (20H, m, —CH$_2$—×10),
1.35–1.46 (2H, m, 7-H, H'),
2.0–2.2 (2H, m, 6-H, H'),
2.944 (1H, m, 2-H),
4.277 (1H, dd, J=12.3, 2.0 Hz, 1-H),
4.501 (1H, dd, J=12.3, 1.5 Hz, 1-H'),
4.882 (1H, dd, J=6.3, 2.0 Hz, 3-H),
5.676 (1H, s,

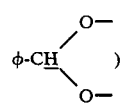

5.75–5.65 (2H, m, 4-H, 5-H),
7.34–7.39 (3H, m, phenyl-H),
7.51–7.54 (2H, m, phenyl-H), Reference Example 6: Preparation of Compound (7) ((2S, 3S)-2-amino-1,3-0-benzylideneoctadecane-1,3-diol)

Method A: A mixture of compound (6) 206.5 mg (0.5 mmol) and 10% Pd-C 20 mg in acetic acid 4 ml was stirred for 24 hr at room temperature under H$_2$. The reaction solution was filtered and the filtrate was evaporated to dryness in vacuo. The resultant pale yellow oil was purified by flush chromatography (11.8 g of Wako gel C-300; eluent: chloroform/methanol=30/1) and then by purification by silica gel TLC to recover 66.5 mg (yield=38.8%) of compound (7) as white powder.

Method B: 413 mg (1 mmole) of compound (6) was dissolved in 10 ml of ethanol, 30 mg of 10% Pd-C was added thereto and the mixture was reacted at room temperature for 5 hours in a stream of hydrogen. The reaction solution was filtered and the filtrate was evaporated to dryness in vacuo to obtain pale yellow powder. The powder was purified by flush chromatography (20.8 g of Wako gel C-300; eluent: chloroform/methanol=19/1) and then recrystallized from n-pentane to recover 336.7 mg (yield=86.6%) of compound (7) as colorless needles.

Physical Properties of Compound (7)

TLC (silica gel/chloroform-methanol (20:1)): Rf=0.41

M.P.=61.5°-62° C.

IR$\nu^{KBr}_{max}$cm$^{-1}$: 2920, 2845, 1460,
1395, 1365, 1150,
1090, 1010

Elemental Analysis (for $C_{25}H_{43}NO_2$), Claculated: C, 77.07; H, 11.12; N, 3.59, Found: C, 77.01; H, 11.30; N, 3.62

$^1$H-NMR (500MHz, CDCl$_3$, TMS)δ:
0.880 (3H, t, J=7.0 Hz, —CH$_3$)
1.20-1.60 (28H, m, —CH$_2$—×14)
2.627 (1H, broad s, 2-H)
3.872 (1H, ddd, J=7.5, 5.7, 1.8 Hz, 3-H)
4.095 (1H, dd, J=11.4, 2.0 Hz, 1-H)
4.147 (1H, dd, J=11.4, 1.5 Hz, 1-H')
5.532 (1H, s,

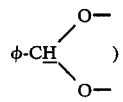

7.32-7.39 (3H, m, phenyl-H)
7.49-7.51 (2H, m, phenyl-H)

Reference Example 7: Preparation of Compound (8) ((2S, 3S)-2-tetracosanamido-1,3-0-benzylidene-octadecane-1,3-diol)

A mixture of compound (7) 316.5 mg (0.82 mmoles), and lignoceric acid 361.8 mg (0.98 mmoles), 2-chloro-1-methylpyridinium iodide 314.3 mg (1.23 mmoles) and tri-n-butylamine 0.78 ml (3.28 mmoles) in 8.2 ml of anhydrous dichloromethane was refluxed for 3 hours in a stream of argon.

The reaction solution was poured into 300 ml of ether, followed by washing with water and saturated NaCl solution and drying over anhydrous magnesium sulfate. The solvent was evaporated off in vacuo and the resultant reddish brown residue was recrystallized from n-pentane to obtain 329.9 mg (yield=54.8%) of colorless needles. The mother liquor of recrystallization was evaporated to dryness in vacuo and the residue was purified by flush chromatography (20 g of Wako gel C-300; eluent: hexane/ethyl acetate=12/1) to obtain 221.5 mg (yield=36.8%, 91.6% in all) of compound (8) as white powder.

Physical properties of Compound (8)

TLC (silica gel/hexane-ethyl acetate (7:3)): Rf=0.32
M.P.=62.5°-63.5° C.

IR$\nu^{KBr}_{max}$cm$^{-1}$: 2920, 2850, 1670,
1490, 1465, 1400,
1370, 1100

Elemental Analysis (for $C_{49}H_{89}NO_3$),
Calculated: C, 79.51; H, 12.12; N, 1.89,
Found: C, 79.25; H, 12.32; N, 1.90

$^1$H-NMR (500MHz, CDCl$_3$, TMS)δ:
0.879 (6H, t, J=7.0 Hz, —CH$_3$×2),
1.20-1.50 (68H, m, —CH$_2$×34),
1.60-1.70 (2H, m, 3'—H, H'),
2.230 (2H, dt, J=2.5, 7.5 Hz, 2'—H, H'),
3.970 (1H, m, 3-H),
4.061 (1H, d, J=10.0 Hz, 2-H),
4.086 (1H, dd, J=11.5, 1.5 Hz, 1-H),
4.130 (1H, dd, J=11.5, 1.5 Hz, 1H'), 5.589 (1H, s,

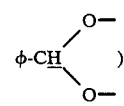

6.166 (1H, d, J=10.0 Hz, NH)

Example 1: Preparation of Compound (A) ((2S, 3S)-2-tetracosanamido-octadecane-1,3-diol)

Compound (8) (22.1 mg; 0.03 mmoles) was dissolved in 1 ml of 1/1 mixture of dichloromethane/methanol, then 0.09 g of Amberlist-15 was added thereto and the mixture was refluxed for 28 hours. The reaction solution was filtered and the filtrate was evaporated to dryness in vacuo. The residue was recrystallized from chloroform to give 14.1 mg (yield=72.4%) of compound (A) as colorless tabular crystals.

Physical Properties of Compound (A)

TLC (silica gel/chloroform-methanol (19:1)): Rf=0.30

M.P.=97.5°-98° C.

IR$\nu^{KBr}_{max}$cm$^{-1}$: 3450, 3360, 2918,
2848, 1611, 1556,
1468, 1383, 1112,
1086

Elemental Analysis (for $C_{42}H_{85}NO_3$),
Calculated: C, 77.36; H, 13.14; N, 2.15,
Found: C, 77.20; H, 13.04; N, 2.17

The NMR (500 MHz) spectrum chart of compound (A) thus obtained were the same as that of compound (A) synthesized through compound (13).

Reference Example 8: Preparation of Compound (9) ((2R, 3S)-2-0-methylsulfonyl-4-octadecene-1,2,3-triol)

To a solution of compound (5) 13.98 g (30 mmol) in ethanol 300 ml, Amberlist-15 was added until the pH of the reaction mixture reached to 4.5 and stirred for 8 hours at 60°to 65° C. The resin in the reaction solution was filtered off, 5 ml of glycerin was added to the filtrate and was evaporated to dryness in vacuo. The resultant residue was purified by flush chromatography (514 g of Wako gel C-300; eluent; hexane/ethyl acetate=4/1) to obtain 8.14 g (yield=71.8%) of compound (9) as white powder.

Physical Properties of Compound (9)

TLC (silica gel/chloroform-methanol (15:1)): Rf=0.31

IR$\nu^{KBr}_{max}$cm$^{-1}$: 3304, 2918, 2848,
1466, 1364, 1349,
1175, 930

Elemental Analysis (for $C_{19}H_{38}O_5S$)
Calculated: C, 60.28; H, 10.12

Found: C, 60.18; H, 10.15

1H-NMR (500 MHz, CDCl3/CD3OD=9/1, TMS)δ:
0.882 (t, J=7.1 Hz, —CH3),
1.2–1.43 (m, —(CH2)n—),
2.059 (q, J=7.0 Hz, 6-H, H'trans),
2.06–2.18 (m, 6-H, H'cis),
3.136 (s, CH3SO2cis),
3.140 (s, CH3SO2trans),
3.779 (dd, J=12.6, 4.0 Hz, 1-Hcis),
3.804 (d, J=6.2 Hz, 1-H, H'trans),
3.842 (dd, J=12.6, 6.6 Hz, 1-H'cis),
4.329 (dd, J=7.3, 4.0 Hz, 3-Htrans),
4.580 (ddd, J=6.6, 4.0, 4.4 Hz, 2-Hcis),
4.607 (dt, J=6.2, 4.0 Hz, 2-Htrans),
4.711 (ddd, J=8.8, 4.4, 1.1 Hz, 3-Hcis),
5.401 (ddd, J=11.0, 8.8, 1.5 Hz, 4-Hcis),
5.477 (ddd, J=15.4 7,3, 1.5 Hz, 4-Htrans),
5.658 (ddd, J=11.0, 7.7, 1.1 Hz, 5-Hcis),
5.804 (ddd, J=15.4, 6.9, 1.1 Hz, 5-Htrans), The ratio of the content of 4-trans-form to that of 4-cis-form of compound (9) was estimated to be 2.7/1.0 from the integrated intensity of NMR peak of 5-H.

Reference Example 9: Preparation of Compound (10)

((2R, 3S)-2-0-methylsulfonyl-1,3-0-bis(1-ethoxyethyl)-4-octadecene-1,2,3-triol)

2.23 g (5.9 mmoles) of compound (9) was dissolved in 13 ml of anhydrous dichloromethane, 3.95 ml (41.3 mmoles) of ethyl vinyl ether and 0.327 g (1.3 mmoles) of pyridinium p-toluenesulfonate were added thereto and they were reacted at room temperature for one hour. Chloroform was added to the reaction solution, followed by washing the solution with saturated NaCl solution, drying over anhydrous magnesium sulfate and distilling off the solvent in vacuo. The resultant yellow oil was purified by flush chromatography (120 g of Kiesel Gel 60, available from Merck Co., Ltd.; eluent: hexane/ethyl acetate=8/2) to obtain 2.98 g (yield=96.8%) of compound (10) as colorless oily product.

Physical Properties of Compound (10)

TLC (silica gel/hexane-ethyl acetate (4:1)): Rf=0.30
IR$\nu^{heat}_{max}$cm$^{-1}$: 2920, 2850, 1465,
1360, 1175, 1130,
1085, 1055, 960,
930

1H-NMR (400 MHz, CDCl3, TMS)δ:
0.879 (t, J=7.0 Hz, —CH3),
1.145–1.227 (m, CH3CH2O×2),
1.279–1.573 (m,

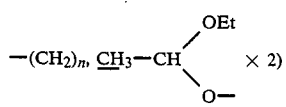

2.052–2.081 (m, 6-H, H'),
3.082–3.105 (m, CH3SO2—),
3.432–3.737 (m, CH3CH2O—×2),
4.692–4.773 (m,

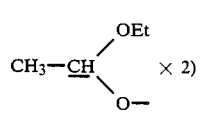

5.30–5.50 (m, 4-Hcis+trans),
5.72–5.83 (m, 5-Hcis+trans),

Reference Example 10: Preparation of Compound (11)

((2S, 3S)-2-azido-1,3-0-bis(1-ethoxyethyl)-4-octadecene-1,3-diol)

Compound (10) (3.72 g; 8.27 mmoles) was dissolved in 58 ml of anhydrous DMF, 3.58 g (49.6 mmoles) of sodium azide was added thereto and the mixture was stirred for 94 hours in an oil bath of 105° to 110° C. The reaction solution was filtered and the filtrate was concentrated in vacuo. The residue was dissolved in ethyl acetate, followed by washing the solution with 10% aqueous solution of sodium hydrogen carbonate, water and then saturated NaCl solution, drying over anhydrous magnesium sulfate and evaporating the solvent off under a reduced pressure. The resulting brown oil was purified by flush chromatography (130 g of Wako gel C-300; eluent: hexane/ethyl acetate=15/1) to obtain 3.28 g (yield =98.1%) of compound (11) as colorless oily substance.

Physical Properties of Compound (11)

TLC (silica gel/hexane-ethyl acetate (4:1)): Rf=0.59
IR$\nu^{heat}_{max}$cm$^{-}$: 2920, 2850, 2100,
1465, 1380, 1270,
1135, 1090, 1055

1H-NMR (500MHz, CDCl3, TMS)δ:
0.880 (t, J=7.0 Hz, —CH3),
1.15–1.22 (m, CH3CH2O—×2),
1.25–1.36 (m,

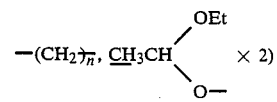

2.04–2.08 (m, 6-H, H'),
3.38–3.79 (m, CH3CH2O—×2),
4.69–4.75 (m,

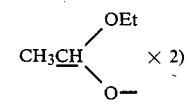

5.27–5.46 (m, 4-Htrans+cis),
5.61–5.76 (m, 5-Htrans+cis),

Reference Example 11: Preparation of Compound (12)

((2S, 3S)-2-amino-1,3-0-bis(1-ethoxyethyl)-octadecane-1,3-diol)

Compound (11) (0.670 g; 1.43 mmoles) was dissolved in 1.43 ml of ethanol, 20 mg of 10% Pd-C was added thereto and the reaction mixture was stirred for 18 hours in hydrogen atomsphere.

The reaction solution was then filtered and the filtrate was evaporated to dryness in vacuo. The resultant oily substance was purified by flush chromatography (32 g of Wako gel C-300; eluent: chloroform containing 1% triethylamine) to give 0.5409 g (yield=85.1%) of compound (12) as colorless oily substance.

Physical Properties of Compound (12)

TLC (silica gel/chloroform-methanol (19:1)): Rf=0.24, 0.32
IR$\nu^{heat}_{max}$cm$^{-1}$: 2920, 2850, 1465,
1375, 1130, 1095, 1055

1H-NMR (500 MHz, CDCl3, TMS)δ:
0.880 (t, J=7.0 Hz, —CH3),
1.17–1.22 (m, CH3CH2O—×2), 1.25–1.58 (m, (CH$_2$)$_n$—),
1.30–1.32 (m,

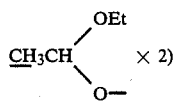

2.94–2.97 (m, 2-H)
3.44–3.52, 3.59–3.67 (m, CH$_3$CH$_2$O×2, 1-H, H', 3-H),
4.68–4.74 (m,

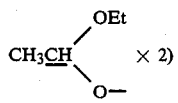

Reference Example 12: Preparation of Compound (13) ((2S, 3S)-2-tetracosanamido-1,3-0-bis(1-ethoxyethy)-octadecane-1,3-diol).

A mixture of compound (12) (486.4 mg; 1.1 mmoles), lignoceric acid (486.6 mg; 1.32 mmoles), 2-chloro-1-methylpyridinium iodide (421.6 mg; 1.65 mmoles) and 1.05 ml (44 mmoles) of tri-n-butylamine in 11 ml of anhydrous dichloromethane was refluxed for one hour and 40 minutes under argon. Ether was added to the reaction solution, the latter was washed with water and then saturated NaCl solution and dried over anhydrous magnesium sulfate, and the solvent thereof was evaporated off in vacuo. The resultant yellow powder was purified by flush chromatography (38 g of Wako gel C-300; eluent: hexane/ethyl acetate=19/1 (containing 0.2% triethylamine)) to obtain 803.0 mg (yield=92.3%) of compound (13) as white powder.

Physical Properties of Compound (13)
TLC (silica gel/hexane-ethyl acetate (7:3)): Rf=0.34
IR$\nu^{heat}_{max}$cm$^{-1}$: 3270, 2920, 2850,
1635, 1540, 1465,
1375, 1130, 1085,
1060
Elemental Analysis (for C$_{50}$H$_{101}$NO$_5$)
Calculated: C, 75.41; H, 12.78; N, 1.76
Found: C, 75.43; H, 12.77; N, 1.75
$^1$H-NMR (500 MHz, CDCl$_3$, TMS)δ:
0.880 (t, J=7.0 Hz, CH$_3$×2),
1.15–1.23 (m, CH$_3$CH$_2$O—×2),
1.20–1.50 (m,

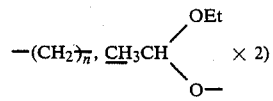

1.60–1.65 (m, 3'-H, H'),
2.167 (t, J=7.5 Hz, 2'-H, H'),
3.44–3.68 (m, CH$_3$CH$_2$—O—×2, 1-H, H'),
3.77–3.81 (m, 3-H),
4.02–4.10 (m, 2-H),
4.65–4.70 (m,

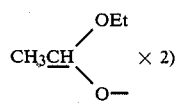

Example 2: Preparation of Compound (A) ((2S, 3S)-2-tetracosanamido-octadecane-1,3-diol)

Compound (13) (663 mg; 0.83 mmoles) was dissolved in 26.5 ml of 1/1 mixed solvent of dichloromethane/methanol, 2.5 g of Amberlist-15 was added thereto and the mixture was stirred at room temperature for 10 hours. The resin in the reaction solution was filtered off and was washed with hot chloroform/methanol solution (9/1). The wash liquid was combined with the filtrate and evaporated to dryness in vacuo. The resultant residue was recrystallized from chloroform to obtain 349.5 mg (yield=64.4%) of colorless tabular crystals. The mother liquor of recrystallization was evaporated to dryness in vacuo, the residue obtained was purified by flush chromatography (8 g of Kiesel Gel 60, available from Merck Co., Ltd.; eluent: chloroform/methanol=29/1) to thereby give 95.9 mg (yield=17.7%) of compound (A) as white powder.

Physical Properties of Compound (A)
TLC (silica gel/chloroform-methanol (19:1)): Rf=0.32
M.P.=98°–98.5° C.
IR$\nu^{KBr}_{max}$cm$^{-1}$: 3450, 3360, 2920,
2850, 1610, 1555,
1465, 1380, 1110,
1085
Elemental Analysis (for C$_{42}$H$_{85}$NO$_3$),
Calculated: C, 77.36; H, 13.14; N, 2.15,
Found: C, 77.15; H, 13.20; N, 2.17
$^1$H-NMR (500 MHz, CDCl$_3$, TMS)δ:
0.884 (6H, t, J=7.0 Hz, CH$_3$×2),
1.20–1.50 (68H, m, CH$_2$×34),
1.60–1.70 (2H, m, 3'-H, H'),
2.243 (2H, t, J=7.5 Hz, 2'-H, H'),
2.397 (1H, t, J=5.3 Hz, 1-OH),
2.525 (1H, d, J=3.3 Hz, 3-OH),
3.83–3.90 (2H, m, 1-H, H'),
3.92–3.96 (2H, m, 2H, 3-H)

Reference Example 13: Preparation of Compound (14) ((2S, 3S)-2-amino-1,3-0-bis(1-ethoxyethyl)-4-octadec-ene-1,3-diol)

Compound (11) (1.30 g; 2.77 mmoles) was dissolved in 40 ml of isopropanol, 0.839 g (22.2 mmoles) of sodium borohydride was added thereto and the solution was refluxed for 48 hours in an oil bath of 100° C. The reaction solution was neutralized with the addition of 30% aqueous solution of acetic acid and then evaporated to dryness in vacuo. The residue was dispersed in water, followed by extracting the dispersion with chloroform, drying the extract over anhydrous magnesium sulfate and concentrated under reduced pressure. The resultant residue was then purified by flush chromatography (65 g of Wako gel C-300; eluent: chloroform containing 1% triethylamine) to obtain 1.16 g (yield=94.5%) of compound (14) as colorless oily product.

Physical Properties of Compound (14)
TLC (silica gel/chloroform-methanol (12:1)): Rf=0.35
IR$\nu^{heat}_{max}$cm$^{-1}$: 2976, 2924, 2854,
1467, 1378, 1340,
1135, 1091, 1058,
1030
Elemental Analysis (for C$_{26}$H$_{53}$NO$_4$/H$_2$O)),
Calculated: C, 67.63; H, 12.01; N, 3.03
Found: C, 67.58; H, 11.84; N, 2.94
$^1$H-NMR (500 MHz, CDCl$_3$, TMS)δ:
0.880 (t, J=7.0 Hz, -CH$_3$),
1.15–1.22 (m, CH$_3$CH$_2$O—×2),
1.61–1.26 (m,

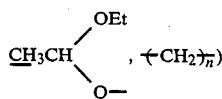

2.053 (q, J=6.9 Hz, 6-H, H')
3.26-3.71 (m, CH$_3$CH$_2$O—×2)
4.64-4.71 (m,

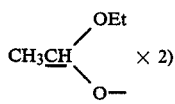

5.20-5.45 (m, 4-Htrans+cis)
5.60-5.70 (m, 5-Htrans+cis)

Example 2: Preparation of Compounds (B) and (C) ((2S, 3S)-2-tetracosanamido-1,3-0-bis(1-ethoxyethyl)-4-octadecene-1,3-diol)

A mixture of compound (14) (132.9 mg; 0.3 mmoles), 132.7 mg (0.36 mmoles) of lignoceric acid, 115.0 mg (0.45 mmoles) of 2-chloro-1-methylpyridinium iodide and 0.29 ml (1.2 mmoles) of tri-n-butylamine in 3 ml of dichloromethane was refluxed for one hour under argon.

Ether was added to the reaction solution, the latter was washed with water and saturated NaCl solution and dried over anhydrous magnesium sulfate and the solvent thereof was distilled off in vacuo. The resultant pale yellow powder was purified by flush chromatography (19 g of Wako gel C-300; eluent: hexane/ethyl acetate=9/1) to obtain 224.9 mg (yield=94.4%) of compounds (B) and (C) as white powder.

Physical Properties of Compound (B) and (C)
TLC (silica gel/hexane-ethyl acetate (7:3)): Rf=0.44
IR$\nu^{KBr}_{max}$cm$^{-1}$: 3296, 2952, 2918,
2850, 1640, 1552,
1471, 1387, 1138,
1036
Elemental Analysis (for C$_{50}$H$_{99}$NO$_5$),
Calculated: C, 75.60; H, 12.56; N, 1.76,
Found: C, 75.43; H, 12.73; N, 1.23
$^1$H-NMR (500 MHz, CDCl$_3$, TMS)
0.866 (t, J=6.9 Hz, CH$_3$×2)
1.16-1.40 (m, —CH$_{2n}$, —CH$_3$CH$_2$O—×2,

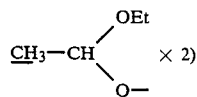

1.55-1.60 (m, 3'-H, H'),
2.00-2.05 (m, 6-H, H'),
2.14-2.20 (m, 2'-H, H'),
3.38-3.68 (m, CH$_3$CH$_2$O—×2),
4.63-4.69 (m,

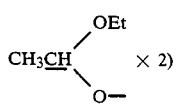

5.29-5.45 (m, 4-Htrans+cis)
5.65-5.86 (m, 5-Htrans+cis)

Reference Example 14: Preparation of Compound (16) ((2S, 3S)-2-tetracosanamido-4-octadecene-1,3-diol)

Compounds (B) and (C) (158.6 mg; 0.2 mmoles) were dissolved in 6.3 ml of 1/1 mixed solvent of dichloromethane/methanol, 0.6 g of Amberlist-15 was added to the reaction solution and the latter was stirred at room temperature for 21 hours. The resin in the solution was filtered off and the resin was washed with hot chloroform. This wash liquid was combined with the foregoing filtrate, the resulting mixture was evaporated to dryness in vacuo, the residue thus obtained was recrystallized from chloroform to obtain 112.8 mg (yield=80.3%) of compound (16) as colorless needles.

Physical Properties of Compound (16)
TLC (silica gel/chloroform-methanol (19:1)): Rf=0.31, 0.39
IR$\nu^{KBr}_{max}$cm$^{-1}$: 3390, 3298, 2954,
2918, 2848, 1645,
1551, 1470, 970,
720
Elemental Analysis (for C$_{42}$H$_{83}$NO$_3$),
Calculated: C, 77.59; H, 12.87; N, 2.15
Found: C, 77.37; H, 12.68; N, 2.32
$^1$H-NMR (500 MHz, CDCl$_3$, TMS)δ:
0.880 (t, J=7.0 Hz, —CH$_3$×2),
1.10-1.40 (m, —CH$_{2n}$),
1.58-1.68 (m, 3'-H, H'),
2.029 (q, J=7.0 Hz, 6-H, H'trans),
2.07-2.13 (m, 6-H, H'cis),
2.20-2.26 (m, 2'-H, H'),
3.78-3.86 (m, 1-H, H'),
3.88-3.95 (m, 2-H, H'),
4.38-4.39 (m, 3-Htrans),
4.60-4.72 (m, 3-Hcis),
5.438 (dtd, J=11.0, 9.1, 1.4 Hz, 4-Hcis),
5.477 (dtd, J=15.4, 6.6, 1.1 Hz, 4-Htrans),
5.749 (ddt, J=15.4, 6.6, 1.1 Hz, 5-Htrans),
7.00 (d, J=7.7 Hz, NH),
7.320 (d, J=7.3 Hz, NH)

The ratio of the content of 4-trans-form to that of 4-cis-form of compound (16) was estimated to be 2.3/1.0 from the integrated intensity of NMR spectra of 5-H.

Example 3: Preparation of Compounds (D) and (E) ((2S, 3S, 4E)-2-tetracosanamido-1,3-di-0-acetyl-4-octadecene-1,3-diol (D) and (2S, 3S, 4Z)-2-tetracosanamido-1,3-di-0-acetyl-4-octadecene-1,3-diol (E))

Compound (16) (102.8 mg; 0.15 mmoles) was dissolved in 5 ml of pyridine, 3 ml of acetic anhydride was added thereto and the reaction was carried out at room temperature for 2 hours. The reaction solution was evaporated to dryness in vacuo and the resultant white powder was purified by flush chromatography (8.59 g of Wako gel C-300; eluent: hexane/ethyl acetate=5/1) to thereby obtain 48.1 mg (yield=41.4%) of compound (D), 21.5 mg (yield=18.5%) of compound (E) and 37.3 mg (yield=32.1%) of the mixture of compounds (D) and (E) as white powder respectively.

Physical Properties of Compound (D)
TLC (silica gel/chloroform-ether (17:1)): Rf=0.36
Elemental Analysis (for C$_{42}$H$_{83}$NO$_3$),
Calculated: C, 75.25; H, 11.94; N, 1.91,
Found: C, 75.10; H, 12.09; N, 1.92
$^1$H-NMR (500 MHz, CDCl$_3$, TMS)δ:
0.880 (6H, t, J=7.0 Hz, —CH$_3$×2),
1.1-1.4 (62H, m, —CH$_2$-×31),
1.55-1.65 (2H, m, 3'-H, H'),
2.018 (2H, q, J=7.0 Hz, 6-H, H'), 2.062 (3H, s, CH$_3$CO—),
2.071 (3H, s, CH$_3$CO—),
2.172 (2H, td, J=7.7, 2.6 Hz, 2'-H, H'),
4.058 (1H, dd, J=11.3, 5.5 Hz, 1-H),
4.089 (1H, dd, J=11.3, 5.5 Hz, 1-H'),
4.416 (1H, m, 2-H),
5.370 (1H, dd, J=14.7, 7.7 Hz, 4-H),
5.403 (1H, dd, J=7.7, 5.5 Hz, 3-H),
5.600 (1H, d, J=9.2 Hz, NH),
5.764 (1H, dt, J=14.7, 7.0 Hz, 5-H)
Physical Properties of Compound (E)
TLC (silica gel/chloroform-ether (17:1)): Rf=0.43
Elemental Analysis (for C$_{46}$H$_{87}$NO$_5$),
Calculated: C, 75.25; H, 11.94; N, 1.91,
Found: C, 75.15; H, 12.10; N, 1.95
$^1$H-NMR (500 MHz, CDCl$_3$, TMS)δ:
0.880 (6H, t, J=7.0 Hz, CH$_3$×2),
1.1–1.4 (62H, m, —CH$_2$—×31),
1.55–1.65 (2H, m, 3'-H, H'),
2.05–2.10 (1H, m, 6-H, H'),
2.050 (3H, s, —COCH$_3$),
2.067 (3H, s, —COCH$_3$),
2.175 (2H, t, J=7.7 Hz, 2'-H, H'),
4.065 (1H, dd, J=11.0, 5.1 Hz, 1-H),
4.102 (1H, dd, J=11.0, 4.7 Hz, 1-H'),
4.401 (1H, m, 2-H),
5.329 (1H, dd, J=10.6, 9.2 Hz, 4-H),
5.644 (1H, d, J=8.8 Hz, NH),
5.679 (1H, dt, J=10.6, 7.7 Hz, 5-H),
5.751 (1H, dd, J=9.2, 6.6 Hz, 3-H), Example 4: Preparation of Compound (F)
((2S, 3S, 4E)-2-tetracosanamido-4-octadecene-1,3-diol)

Compound (D) (39.6 mg; 0.052 mmoles) was dissolved in 2 ml of 1/1 mixed solvent of methanol/THF, 155 ml (0.155 mmoles) of 1N sodium methoxide (methanol solution) was added thereto and the reaction was carried out at room temperature for 2 hours. The reaction solution was neutralized with DOWEX 50W×8 (H-type) and the resin was filtered off and then was washed with hot chloroform. This washing was combined with the foregoing filtrate and the mixture was evaporated to dryness in vacuo. The resultant residue was washed with methanol and was recrystallized from chloroform to thus obtain 32.5 mg (yield=92.7%) of compound (F) as colorless needles.
Physical Properties of Compound (F)
TLC (silica gel/chloroform-methanol (19:1)): Rf=0.31
Elemental Analysis (for C$_{46}$H$_{83}$NO$_3$),
Calculated: C, 77.59; H, 12.87; N, 2.15,
Found: C, 77.53; H, 12.80; N, 2.18
$^1$H-NMR (500 MHz, CDCl$_3$/CD$_3$OD=9/1, TMS)δ:
0.882 (6H, t, J=6.6 Hz, CH$_3$×2),
1.2–1.4 (62H, m, —CH$_2^-$×31),
1.55–1.65 (2H, m, 3'H, H'),
2.021 (2H, q, J=7.0 Hz, 6-H, H'),
2.204 (2H, t, J=7.7 Hz, 2'-H, H'),
3.654 (2H, d, J=5.5 Hz, 1-H, H'),
3.817 (1H, dt, J=3.3, 5.5 Hz, 2-H),
4.351 (1H, m, 3H),
5.427 (1H, ddt, J=15.4, 6.2, 1.3 Hz, 4-H),
5.729 (1H, dtd, J=15.4, 6.6, 1.1 Hz, 5-H)

Example 5: Preparation of Compound (G)
((2S, 3S, 4Z)-2-tetracosanamido-4-octadecene-1,3-diol)

Compound (E) (15.6 mg; 0.020 mmoles) was dissolved in 1 ml of 1/1 mixed solvent of methanol/THF, 61 micro liters (0.061 mmoles) of 1N sodium methoxide (methanol solution) was added thereto and the reaction was carried out at room temperature for 2 hours. The reaction solution was neutralized with DOWEX 50W×8 (H-type), then the resin was filtered off and the resin was washed with hot chloroform. This was liquid was combined with the foregoing filtrate and the mixture was evaporated to dryness in vacuo. The resultant residue was washed with methanol and was recrystallized from chloroform to thus obtain 12.0 mg (yield=86.9%) of compound (G) as colorless needles.
Physical Properties of Compound (G)
TLC (silica gel/chloroform-methanol (19:1)): Rf=0.39
IRν$^{KBr}_{max}$cm$^{-1}$: 3388, 3294, 2918,
2848, 1648, 1538,
1464, 1024,
Elemental Analysis (for C$_{42}$H$_{83}$NO$_3$),
Calculated: C, 77.59; H, 12.87; N, 2.15,
Found: C, 77.55; H, 12.93; N, 2.17
$^1$H-NMR (500 MHz, CDCl$_3$/CD$_3$OD=9/1, TMS)δ:
0.882 (6H, t, J=6.9 Hz, CH$_3$—×2),
1.20–1.40 (62H, m, —CH$_2$—×31),
1.55–1.65 (2H, m, 3'-H, H'),
2.02–2.15 (2H, m, 6-H, H'),
2.223 (2H, t, J=7.7 Hz, 2'H, H'),
3.632 (1H, dd, J=12.1, 5.5 Hz, 1-H),
3.651 (1H, dd, J=12.1, 5.5 Hz, 1-H'),
3.794 (1H, dt, J=3.3, 5.5 Hz, 2-H),
4.671 (1H, ddd, J=8.8, 3.3, 1.0 Hz, 3-H),
5.396 (1H, ddt, J=11.0, 8.8, 1.3 Hz, 4-H),
5.548 (1H, dtd, J=11.0, 7.7, 1.0 Hz, 5-H)

What is claimed is:

1. An unnatural ceramide related compound represented by the formulas (I) or (II):

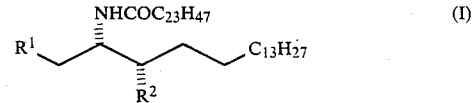

(I)

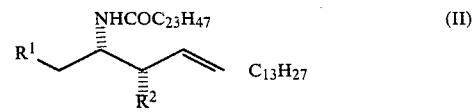

(II)

wherein R$^1$ and R$^2$ are independently hydroxyl group, acetoxy group or 1-ethoxyethyloxy group.

2. A compound according to claim 1 wherein the compound represented by the formula (I) is (A) (2S, 3S)-2-tetracosanamido-octadecane-1,3-diol.

3. A compound according to claim 1 wherein the compound represented by the formula (II) is one member selected from the group consisting of (B) (2S, 3S, 4E)-2-tetracosanamido-1,3-0-bis(1-ethoxyethyl)-4-octadecene-1,3-diol; (C) (2S, 3S, 4Z)-2-tetracosanamido-1,3-0-bis(1-ethoxyethyl)-4-octadecene-1,3-diol; (D) (2S, 3S, 4E)-2-tetracosanamido-1,3-di-0-acetyl-4-octadecene-1,3-diol; (E) (2S, 3S, 4Z)-2-tetracosanamido-1,3-di-0-acetyl-4-octadecene-1,3-diol; (F) (2S, 3S, 4E)-2-tetracosanamido-4-octadecene-1,3-diol; and (G) (2S, 3S, 4Z)-2-tetracosanamido-4-octadecene-1,3-diol.

4. A method for preparing an unnatural ceramide related compound ((2S, 3S)-2-tetracosanamido-octadecane-1,3-diol) represented by the formula:

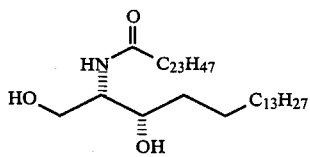

comprises subjecting a compound represented by the formula

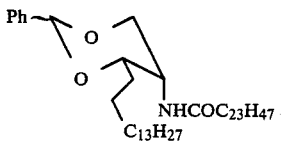

to deacetal treatment.

5. A method according to claim 4 wherein p-toluenesulfonic acid, hydrochloric acid or Amberlist-15 is used as a catalyst.

6. A method according to claim 4 wherein the catalyst is Amberlist-15.

7. A method according to claim 4 wherein the reaction is carried out at the reflux temperature of dichloromethane/methanol, chloroform/methanol or tetrahydrofuran/methanol for about 5 to about 30 hours.

8. A method according to claim 4 wherein compound (8) is prepared by reacting a compound represented by the formula (7):

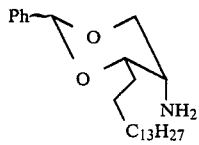

with lignoceric acid.

9. A method according to claim 8 wherein the reaction is carried out in dichloromethane, chloroform or dichloroethane, at the reflux temperature of the solvent for about 0.5 to 13 hours.

10. A method for preparing (2S, 3S)-2-tetracosanamido-octadecane-1,3-diol represented by the formula:

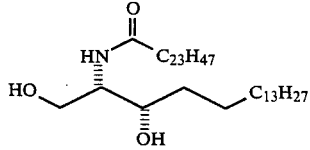

comprises subjecting a compound represented by the formula:

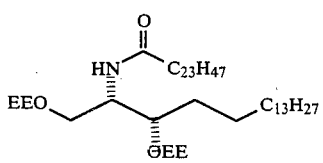

(wherein EE represents a 1-ethoxyethyl group) to deethoxyethylation.

11. A method according to claim 10 wherein the reaction is carried out in dichloromethane/methanol, chloroform/methanol or tetrahydrofuran/methanol in the presence of Amberlist-15 or p-toluenesulfonic acid.

12. A method according to claim 11 wherein the reaction is carried out at about 0° to about 30° C. for about 5 to about 20 hours.

13. A method according to claim 10 wherein compound (13) is prepared by reacting a compound represented by the formula (12):

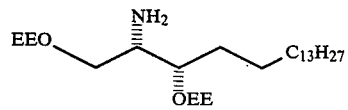

with lignoceric acid.

14. A method according to claim 13 wherein the reaction is carried out in dichloromethane, chloroform or dichloroethane, at the reflux temperature of the solvent for about 0.5 to 13 hours.

15. A method for preparing (2S, 3S, 4E)-2-tetracosanamido-4-octadecene-1,3-diol represented by the formula:

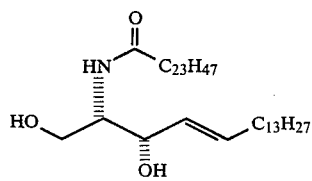

and (2S, 3S, 4Z)-2-tetracosanamido-4-octadecene-1,3-diol represented by the formula:

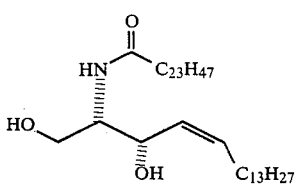

comprises acetylating (2S, 3S)-2-tetracosanamido-4-octadecene-1,3-diol represented by the formula:

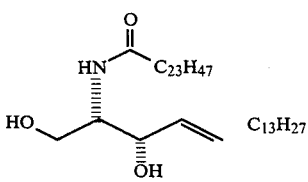

to protecting the same, then separating the products into (2S, 3S, 4E)-2-tetracosanamido-1,3-di-0-acetyl-4-octadecene-1,3-diol represented by the formula:

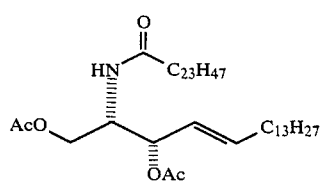

and (2S, 3S, 4Z)-2-tetracosanamido-1,3-di-0-acetyl-4-octadecene-1,3-diol represented by the formula:

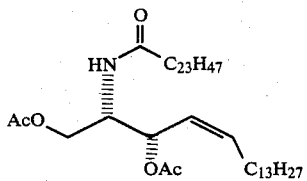
(E)

and then deacetylating these products.

16. A method according to claim 15 wherein compound (16) is prepared by eliminating protective groups from (2S, 3S, 4E)-2-tetracosanamido-1,3-0-bis(1-ethoxyethyl)-4-octadecene-1,3-diol and (2S, 3S, 4Z)-2-tetracosanamido-1,3-0-bis(1-ethoxyethyl)-4-octadecene-1,3-diol.

17. A method according to claim 16 wherein the elimination reaction is carried out in dichloromethane/methanol, chloroform/methanol or tetrahydrofuran/methanol at about 0° to about 30° C. for about 5 to about 24 hours in the presence of Amberlist-15 or p-toluenesulfonic acid.

* * * * *

UNITED STATES PATENT AND TRADEMARK OFFICE
CERTIFICATE OF CORRECTION

PATENT NO. : 4,880,572

DATED : November 14, 1989

INVENTOR(S) : Shuji Fujita, Shoji Yoshimura, Masayoshi Ito, Yoshiyasu Shitori and Tomoya Ogawa It is certified that error appears in the above-identified patent and that said Letters Patent is hereby corrected as shown below:

On the title page:

In item [30] change the Japanese Priority Application to read --62-132696--.

Signed and Sealed this

Second Day of July, 1991

Attest:

Attesting Officer

HARRY F. MANBECK, JR.

Commissioner of Patents and Trademarks